United States Patent
Minagawa

(10) Patent No.: US 10,954,352 B2
(45) Date of Patent: Mar. 23, 2021

(54) SURFACE MODIFICATION METHOD AND SURFACE-MODIFIED ELASTIC BODY

(71) Applicant: Sumitomo Rubber Industries, Ltd., Kobe (JP)

(72) Inventor: Yasuhisa Minagawa, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 31 days.

(21) Appl. No.: 16/370,205

(22) Filed: Mar. 29, 2019

(65) Prior Publication Data

US 2019/0315900 A1    Oct. 17, 2019

(30) Foreign Application Priority Data

Apr. 13, 2018   (JP) ............................... JP2018-077832
Oct. 15, 2018   (JP) ............................... JP2018-194294

(51) Int. Cl.

| | |
|---|---|
| *C08J 7/16* | (2006.01) |
| *C08F 279/02* | (2006.01) |
| *A61M 5/315* | (2006.01) |
| *C08F 2/48* | (2006.01) |
| *C08F 8/20* | (2006.01) |
| *C08F 236/10* | (2006.01) |
| *C08L 15/02* | (2006.01) |
| *C08C 19/25* | (2006.01) |

(52) U.S. Cl.
CPC ............. *C08J 7/16* (2013.01); *A61M 5/31513* (2013.01); *C08F 2/48* (2013.01); *C08F 8/20* (2013.01); *C08F 236/10* (2013.01); *C08F 279/02* (2013.01); *C08L 15/02* (2013.01); *A61M 2205/0222* (2013.01); *C08C 19/25* (2013.01)

(58) Field of Classification Search
CPC .................................. C08J 7/16; C08F 279/02
See application file for complete search history.

(56) References Cited

U.S. PATENT DOCUMENTS

| | | | | |
|---|---|---|---|---|
| 2013/0053786 A1* | 2/2013 | Maeda | ................ | B29C 33/3842 604/187 |
| 2015/0273155 A1* | 10/2015 | Kaneko | .............. | B29D 99/0053 604/222 |
| 2016/0376414 A1* | 12/2016 | Minagawa | ................. | C08J 7/00 522/46 |
| 2018/0036490 A1* | 2/2018 | Minagawa | ............... | F16J 15/56 |

FOREIGN PATENT DOCUMENTS

| | | |
|---|---|---|
| JP | 2004-298220 A | 10/2004 |
| JP | 2010-142573 A | 7/2010 |
| JP | 2016-209081 | * 12/2016 |

OTHER PUBLICATIONS

Machine translation of JP 2016-209081 into English (no date).*
"Roughness Parameters" printed from the Robert and Co. Ltd. internet site (no date).*

* cited by examiner

Primary Examiner — Marc S Zimmer
(74) Attorney, Agent, or Firm — Birch, Stewart, Kolasch & Birch, LLP

(57) ABSTRACT

Provided are methods for surface-modifying a rubber vulcanizate and surface-modified elastic bodies, which can cost-effectively provide a variety of functions, including sliding properties, liquid leakage resistance, and protein adsorption resistance. Included is a method for surface-modifying a rubber vulcanizate as a modification target, the method including: step 1 of forming polymerization initiation points A on the surface of the modification target; step 2 of radically polymerizing a monomer starting from the polymerization initiation points A to grow polymer chains; and step 3 of adding a silane compound to the surfaces of the polymer chains, followed by reaction with at least a fluoroalkyl group-containing silane compound to form modified polymer chains.

13 Claims, 1 Drawing Sheet

SURFACE MODIFICATION METHOD AND SURFACE-MODIFIED ELASTIC BODY

TECHNICAL FIELD

The present invention relates to surface modification methods and surface-modified elastic bodies such as gaskets for syringes at least part of whose surface is modified by any of the modification methods.

BACKGROUND ART

In view of the importance of sealing properties (liquid leakage resistance), elastic bodies such as rubber are used in parts which slide while maintaining a seal, e.g., a gasket which is integrated with a plunger of a syringe to form a seal between the plunger and the barrel. Unfortunately, such elastic bodies have a slight problem with sliding properties (see Patent Literature 1). To address this problem, a sliding property-improving agent, for example silicone oil, may be applied to the sliding surface; however, a concern has been raised over the potential adverse effects of silicone oil on recently marketed bio-preparations. On the other hand, gaskets not coated with a sliding property-improving agent have inferior sliding properties and therefore do not allow plungers to be smoothly pushed but cause them to pulsate during administration. This can result in problems such as inaccurate injection amounts and infliction of pain on patients.

To satisfy the conflicting requirements, i.e. sealing properties and sliding properties, a method of coating surfaces with a self-lubricating PTFE film has been proposed (see Patent Literature 2). Unfortunately, such PTFE films are generally expensive and thus will increase the production cost of processed products, limiting the range of application of the method. Moreover, products coated with PTFE films might be unreliable when they are used in applications where sliding or similar movement is repeated and durability is therefore required. Still another problem is that since PTFE is vulnerable to radiation, PTFE-coated products cannot be sterilized by radiation.

Consideration may also be given to the use in other applications where sliding properties are required in the presence of water. Specifically, water can be delivered without a loss by reducing the fluid resistance of the inner surface of a pre-filled syringe or of the inner surface of a pipe or tube for delivering water, or by increasing or markedly reducing the contact angle with water thereof. Reducing the surface resistance of the internal/external surface of a catheter tube may facilitate insertion of the catheter into the body or introduction of a guide wire through the catheter. Increasing the contact angle with water of the surface of a medical device may reduce adhesion of specific cells (blood cells) and proteins in blood or body fluid. Drainage of water on wet roads or of snow on snowy roads can be improved by reducing the fluid resistance of the groove surfaces of tires, or by increasing or markedly reducing the contact angle with water thereof. This can result in improved grip performance and hydroplaning performance and thus better safety. In addition, less adhesion of dirt and dust can be expected when the sliding resistance of the sidewall surfaces of tires or the walls of buildings is reduced, or when the contact angle with water thereof is increased.

Further advantageous effects can be expected, including, for example: less pressure loss upon delivering liquid such as water or an aqueous solution through a diaphragm such as a diaphragm pump or valve; easy sliding of skis and snowboards achieved by enhancing the sliding properties of the sliding surfaces thereof; better noticeability of road signs and signboards achieved by enhancing the sliding properties thereof to allow snow to readily slide on the surface; reduction in water resistance or drag on the outer peripheries of ships and less adhesion of bacteria to these outer peripheries achieved by reducing the sliding resistance of the outer peripheries or by increasing the contact angle with water thereof; and reduction in water resistance or drag of swimsuits achieved by improving the sliding properties of the thread surfaces thereof.

CITATION LIST

Patent Literature

Patent Literature 1: JP 2004-298220 A
Patent Literature 2: JP 2010-142573 A

SUMMARY OF INVENTION

Technical Problem

The present invention aims to solve the above problems and provide methods for surface-modifying a rubber vulcanizate and surface-modified elastic bodies, which can cost-effectively provide a variety of functions, including sliding properties, liquid leakage resistance, and protein adsorption resistance.

Solution to Problem

The present invention relates to a method for surface-modifying a rubber vulcanizate as a modification target, the method including:

step 1 of forming polymerization initiation points A on a surface of the modification target;

step 2 of radically polymerizing a monomer starting from the polymerization initiation points A to grow polymer chains; and step 3 of adding a silane compound to surfaces of the polymer chains, followed by reaction with at least a fluoroalkyl group-containing silane compound to form modified polymer chains.

Preferably, step 3 includes adding a silane compound to surfaces of the polymer chains, followed by reaction with at least a fluoroalkyl group-containing silane compound and a perfluoroether group-containing silane compound to form modified polymer chains.

The present invention also relates to a method for surface-modifying a rubber vulcanizate as a modification target, the method including:

step I of radically polymerizing a monomer in the presence of a photopolymerization initiator A on a surface of the modification target to grow polymer chains; and step II of adding a silane compound to surfaces of the polymer chains, followed by reaction with at least a fluoroalkyl group-containing silane compound to form modified polymer chains.

Preferably, step II includes adding a silane compound to surfaces of the polymer chains, followed by reaction with at least a fluoroalkyl group-containing silane compound and a perfluoroether group-containing silane compound to form modified polymer chains.

Preferably, the fluoroalkyl group-containing silane compound and the perfluoroether group-containing silane compound are combined in a ratio of 50:50 to 100:0.

Preferably, the fluoroalkyl group is represented by the following formula:

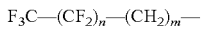

wherein n is an integer of 0 to 5 and m is an integer of 0 to 8.

Preferably, the rubber vulcanizate has a Shore A hardness of 50 to 70, more preferably 53 to 65.

Preferably, the monomer is at least one selected from the group consisting of acrylic acid, acrylic acid esters, alkali metal salts of acrylic acid, amine salts of acrylic acid, acrylamide, dimethylacrylamide, diethylacrylamide, isopropylacrylamide, hydroxyethylacrylamide, acryloylmorpholine, methoxymethyl acrylate, hydroxyethyl acrylate, methacrylic acid, methacrylic acid esters, alkali metal salts of methacrylic acid, amine salts of methacrylic acid, methacrylamide, dimethylmethacrylamide, diethylmethacrylamide, isopropylmethacrylamide, hydroxyethylmethacrylamide, methacryloylmorpholine, methoxymethyl methacrylate, hydroxyethyl methacrylate, and acrylonitrile.

Preferably, the fluoroalkyl group-containing silane compound is represented by the following formula (1):

$$F_3C-(CF_2)_n-(CH_2)_m-Si(OR^1)_3 \quad (1)$$

wherein n is 0 to 5; m is 0 to 8; and each $R^1$ may be the same or different and represents an alkyl group.

Preferably, the perfluoroether group-containing silane compound is represented by the following formula (2) or (3):

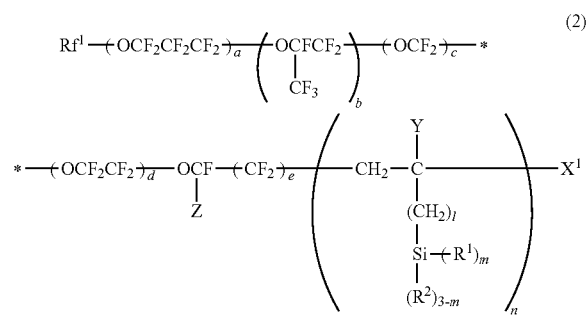

wherein $Rf^1$ is a perfluoroalkyl group; Z is fluorine or a trifluoromethyl group; a, b, c, d, and e are the same as or different from each other and each represent an integer of 0 or 1 or more, provided that a+b+c+d+e is 1 or more and the order of the repeating units parenthesized by subscripts a, b, c, d, and e occurring in the formula is not limited to that shown; Y is hydrogen or a C1-C4 alkyl group; $X^1$ is hydrogen, bromine, or iodine; $R^1$ is a hydroxy group or a hydrolyzable substituent; $R^2$ is hydrogen or a monovalent hydrocarbon group; l is 0, 1, or 2; m is 1, 2, or 3; and n is an integer of 1 or more, provided that the two ends marked by * are directly bonded to each other, or

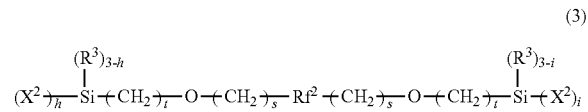

wherein $Rf^2$ is a divalent group that contains a unit represented by $-(C_kF_{2k})O-$ where k is an integer of 1 to 6, and has a non-branched linear perfluoropolyalkylene ether structure; each $R^3$ is the same or different and represents a C1-C8 monovalent hydrocarbon group; each $X^2$ is the same or different and represents a hydrolyzable group or a halogen atom; each s is the same or different and represents an integer of 0 to 2; each t is the same or different and represents an integer of 1 to 5; and h and i are the same as or different from each other and each represent 1, 2, or 3.

Preferably, the modified polymer chains have a length of 200 to 7000 nm.

The present invention also relates to a surface-modified elastic body, including a three-dimensional solid body at least part of whose surface is modified by the method.

The present invention also relates to a gasket for syringes, at least part of whose surface is modified by the method.

Preferably, the gasket for syringes includes a gasket base material with the polymer chains fixed on at least part of a surface thereof, the gasket has a sliding surface provided with a plurality of annular projections, the annular projections include a first projection nearest to a top surface of the gasket, and the first projection has a surface roughness Ra of not greater than 1.0.

Preferably, the surface roughness Ra is not greater than 0.8, more preferably not greater than 0.6.

Preferably, the gasket base material has a surface roughness Ra of not greater than 1.0, more preferably not greater than 0.8, still more preferably not greater than 0.6.

Preferably, the gasket for syringes includes a gasket base material with the polymer chains fixed on at least part of a surface thereof, the gasket has a sliding surface provided with a plurality of annular projections, the annular projections include a first projection nearest to a top surface of the gasket, and the first projection has a surface roughness Rz of not greater than 25.0.

Preferably, the gasket for syringes includes a gasket base material with the polymer chains fixed on at least part of a surface thereof, the gasket has a sliding surface provided with a plurality of annular projections, the annular projections include a first projection nearest to a top surface of the gasket, and the first projection has a surface roughness Rv of not greater than 21.0.

Advantageous Effects of Invention

The surface modification methods of the present invention which include steps 1 to 3 or steps I and II can cost-effectively provide a variety of functions, including sliding properties, liquid leakage resistance, and protein adsorption resistance.

DESCRIPTION OF EMBODIMENTS

Figure 1:
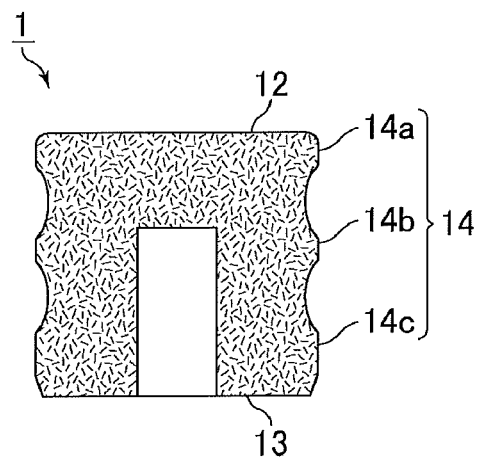
FIG. 1 is an example of a longitudinal sectional view of a gasket base material on which modified polymer chains are to be fixed.

A first aspect of the present invention relates to a method for surface-modifying a rubber vulcanizate as a modification target, which includes: step 1 of forming polymerization initiation points A on the surface of the modification target; step 2 of radically polymerizing a monomer starting from the polymerization initiation points A to grow polymer chains; and step 3 of adding a silane compound to the surfaces of the polymer chains, followed by reaction with at least a fluoroalkyl group-containing silane compound to form modified polymer chains.

To provide desired functions by forming polymer chains on the surface of a rubber vulcanizate which is generally very rough, it is necessary to form polymer chains having a certain height (length) from the surface while disposing functional polymer chains on the top. However, the use of functional monomers, which are usually very expensive, is economically disadvantageous unless the amount of polymer chains formed from these monomers is limited to the minimum required to produce the desired functions. In contrast, the present invention provides a surface modification method that includes first forming polymer chains from relatively inexpensive monomers on the surface of a modification target to build a scaffold of a certain size, adding a silane compound onto the scaffold, and further reacting (e.g. adding) at least a fluoroalkyl group-containing silane compound with the silane compound to form modified polymer chains, whereby the fluoroalkyl group-containing functional silane compound is provided on the outermost surface. Thus, desired functions can be provided very cost-effectively. It should be noted that desired properties such as sufficient sliding properties cannot be obtained by providing a fluoroalkyl group-containing functional silane compound alone, without forming relatively inexpensive polymer chains.

Moreover, since modified polymer chains are formed in which a fluoroalkyl group-containing silane compound with low surface free energy is provided on the outermost surface, high properties such as sliding properties, liquid leakage resistance, biocompatibility, and protein adsorption resistance can be imparted to the modification target. It should be noted that perfluoroether groups also have low surface free energy but contain ether oxygen, whereas according to the present invention, an oxygen-free fluoroalkyl group is dominantly provided on the surface, which can provide higher properties such as liquid leakage resistance, biocompatibility, and protein adsorption resistance.

Step 1 includes forming polymerization initiation points A on the surface of a vulcanized rubber (modification target). The rubber vulcanizate may suitably contain a carbon atom adjacent to a double bond (i.e., allylic carbon atom).

Examples of rubbers that can be used as the modification target include diene rubbers such as styrene-butadiene rubber, polybutadiene rubber, polyisoprene rubber, natural rubber, and deproteinized natural rubber; and butyl rubber and halogenated butyl rubber which have a degree of unsaturation of a few percent of isoprene units. The butyl rubber or halogenated butyl rubber, if used, is preferably a rubber crosslinked by triazine because the amount of matter extracted from the rubber vulcanizate is reduced. In this case, the rubber may contain an acid acceptor. Suitable examples of the acid acceptor include hydrotalcite and magnesium carbonate.

If other rubbers are used, preferably sulfur vulcanization is performed. In such cases, compounding ingredients commonly used in sulfur vulcanization may be added, such as vulcanization accelerators, zinc oxide, fillers, and silane coupling agents. Suitable examples of the fillers include carbon black, silica, clay, talc, and calcium carbonate.

The vulcanization conditions of the rubber used may be selected appropriately. The rubber is preferably vulcanized at a temperature of 150° C. or higher, more preferably 170° C. or higher, still more preferably 175° C. or higher.

In view of functions such as sliding properties, liquid leakage resistance, and protein adsorption resistance, the rubber vulcanizate preferably has a Shore A hardness of 50 to 70, more preferably 53 to 65.

The hardness of the rubber vulcanizate is determined using a type-A durometer (Shore A) at 23° C. according to JIS K 6253.

The formation of polymerization initiation points A may be accomplished, for example, by adsorbing a photopolymerization initiator A onto the surface of the modification target. Examples of the photopolymerization initiator A include carbonyl compounds, organic sulfur compounds such as tetraethylthiuram disulfide, persulfides, redox compounds, azo compounds, diazo compounds, halogen compounds, and photoreductive pigments. Carbonyl compounds are especially preferred.

Preferred examples of carbonyl compounds which can be used as the photopolymerization initiator A include benzophenone and derivatives thereof (benzophenone compounds). Thioxanthone compounds may also be suitable as the photopolymerization initiator A because they provide a high polymerization rate and also readily adsorb onto and/or react with rubber or other similar material. In particular, it is preferred to use at least one benzophenone compound. Examples of the benzophenone or thioxanthone compounds include those disclosed in WO 2016/042912, which is hereby incorporated by reference.

The photopolymerization initiator A such as a benzophenone or thioxanthone compound may be adsorbed onto the surface of the modification target, e.g. as described in WO 2016/042912, which is hereby incorporated by reference.

In particular, the formation of polymerization initiation points A may be carried out by treating the surface of the modification target with the photopolymerization initiator A so that the photopolymerization initiator A is adsorbed onto the surface, optionally followed by irradiating the treated surface with LED light having a wavelength of 300 to 400 nm. More specifically, it may be carried out by treating the surface of the modification target with a solution of a benzophenone or thioxanthone compound so that the photopolymerization initiator A is adsorbed, optionally followed by irradiating the treated surface with LED light having a wavelength of 300 to 400 nm so that the adsorbed photopolymerization initiator A is chemically bonded to the surface. Since light having a wavelength of less than 300 nm may break and damage the molecules in the modification target, light having a wavelength of 300 nm or more is preferably used. Light having a wavelength of 355 nm or more is more preferred in that such light causes only very small damage to the modification target. However, since light having a wavelength of more than 400 nm is less able to activate the polymerization initiator and does not allow the polymerization reaction to proceed readily, light having a wavelength of 400 nm or less is preferred. LED light having a wavelength of 355 to 390 nm is particularly suitable. Although LED light is suitable in that the wavelength range of LED light is narrow so that no wavelengths other than the center wavelength are emitted, mercury lamps or other light sources can also produce similar effects to LED light by using a filter to block light with wavelengths less than 300 nm.

Step 2 includes radically polymerizing a monomer starting from the polymerization initiation points A to grow polymer chains.

The monomer used in step 2 is intended to form polymer chains which do not have functions chosen appropriately according to, for example, the application. For example, in cases where it is desired to impart functions such as sliding properties, biocompatibility, and anti-bacterial properties to the modification target, the monomer corresponds to a monomer which does not provide such functions and may be appropriately selected in view of economic efficiency, for example.

The monomer may be selected appropriately from the above-mentioned standpoint. Examples of such monomers include acrylic acid, acrylic acid esters such as methyl acrylate and ethyl acrylate, alkali metal salts of acrylic acid such as sodium acrylate and potassium acrylate, amine salts of acrylic acid, acrylamide, dimethylacrylamide, diethylacrylamide, isopropylacrylamide, hydroxyethylacrylamide, acryloylmorpholine, methoxymethyl acrylate, hydroxyethyl acrylate, methacrylic acid, methacrylic acid esters such as methyl methacrylate and ethyl methacrylate, alkali metal salts of methacrylic acid such as sodium methacrylate and potassium methacrylate, amine salts of methacrylic acid, methacrylamide, dimethylmethacrylamide, diethylmethacrylamide, isopropylmethacrylamide, hydroxyethylmethacrylamide, methacryloylmorpholine, methoxymethyl methacrylate, hydroxyethyl methacrylate, and acrylonitrile. These may be used alone or in combinations of two or more. Preferred among these are (meth)acrylic acid and/or (meth)acrylamide, with combinations of (meth)acrylic acid with (meth)acrylamide being more preferred.

The method for radical polymerization of the monomer and the amount of the monomer, the solvent for application (spraying), the method for application (spraying), the method for immersion, the conditions for irradiation, and other conditions used in step 2 may be those described in WO 2016-042912, which is hereby incorporated by reference. Furthermore, a solution of the monomer or the liquid monomer may contain a known polymerization inhibitor such as 4-methylphenol.

In the present invention, the radical polymerization of the monomer may be allowed to proceed by light irradiation after the modification target is subjected to application of or immersion in a solution of the monomer or the liquid monomer and optionally then taken out and dried. Here, UV light sources with an emission wavelength mainly in the ultraviolet region, such as high-pressure mercury lamps, metal halide lamps, and LED lamps, can be suitably used. The light dose may be appropriately selected in view of polymerization time and uniform reaction progress. In order to prevent inhibition of polymerization due to active gases such as oxygen in the reaction vessel, oxygen is preferably removed from the reaction vessel and the reaction solution during or before the light irradiation. For this purpose, appropriate operations may be performed. For example, an inert gas such as nitrogen gas or argon gas may be inserted into the reaction vessel and the reaction solution to discharge active gases such as oxygen from the reaction system and thereby replace the atmosphere in the reaction system with the inert gas. Or the reaction vessel may be evacuated to remove oxygen. Also, in order to prevent inhibition of the reaction due to oxygen and other gases, an appropriate measure may be taken; for example, an UV light source may be placed such that an air layer (oxygen content: 15% or higher) does not exist between the reaction vessel made of glass, plastic, or other material and the reaction solution or the modification target.

In the case of irradiation with ultraviolet light, the ultraviolet light preferably has a wavelength of 300 to 400 nm. Such light allows polymer chains to be formed well on the surface of the modification target. The light source used may be, for example, a high-pressure mercury lamp, an LED with a center wavelength of 365 nm, or an LED with a center wavelength of 375 nm. In particular, irradiation with LED light having a wavelength of 355 to 390 nm is preferred. LEDs or other light sources that have a center wavelength of 365 nm, which is close to the excitation wavelength (366 nm) of benzophenone, are particularly preferred in view of efficiency.

Step 3 includes adding a silane compound to the surfaces of the polymer chains, followed by reaction with a fluoroalkyl group-containing silane compound to form (prepare) modified polymer chains. Thus, modified polymer chains in which a fluoroalkyl group-containing functional silane compound is added to the surfaces of the polymer chains may be formed to provide desired properties.

Non-limiting examples of the silane compound include silane compounds free from fluoroalkyl groups. In particular, in order to better achieve the effects of the present invention, alkoxysilanes and modified alkoxysilanes are preferred, with alkoxysilanes being more preferred. These silane compounds may be used alone or in combinations of two or more.

Examples of the alkoxysilanes include monoalkoxysilanes such as trimethylmethoxysilane, triethylethoxysilane, tripropylpropoxysilane, and tributylbutoxysilane; dialkoxysilanes such as dimethyldimethoxysilane, diethyldiethoxysilane, dipropyldipropoxysilane, and dibutyldibutoxysilane; trialkoxysilanes such as methyltrimethoxysilane, ethyltriethoxysilane, propyltripropoxysilane, and butyltributoxysilane; and tetraalkoxysilanes such as tetramethoxysilane, tetraethoxysilane, tetrapropoxysilane, tetrabutoxysilane, dibutoxydiethoxysilane, butoxytriethoxysilane, and ethoxytriethoxysilane. These may be used alone or in combinations of two or more. In order to better achieve the effects of the present invention, tetraalkoxysilanes are preferred among these, with tetramethoxysilane, tetraethoxysilane, tetrabutoxysilane, dibutoxydiethoxysilane, butoxytriethoxysilane, and ethoxytributoxysilane being more preferred.

The term "modified alkoxysilane" refers to an alkoxysilane having a substituent such as an amino, carboxyl, hydroxy, or epoxy group, and preferably contains at least one selected from the group consisting of alkyl, amino, carboxyl, hydroxy, and epoxy groups.

In order to better achieve the effects of the present invention, alkoxysilanes and modified alkoxysilanes each having a carbon number of 4 to 22, preferably 4 to 16, are preferred.

In order to better achieve the effects of the present invention, alkoxysilanes and modified alkoxysilanes each containing at least one selected from the group consisting of methoxy, ethoxy, propoxy, and butoxy groups, preferably ethoxy and/or butoxy groups, still more preferably ethoxy and butoxy groups, are preferred.

Commercial products of the silane compound include Primer coat PC-3B (Fluoro Technology, the butoxy/ethoxy tetraalkoxysilane represented by the following formula):

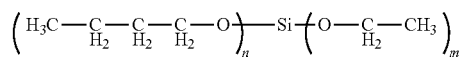

wherein m+n=4 with n>m>0 on average.

In step 3, the silane compound may be added to the surfaces of the polymer chains by any method, and appropriate conventional methods may be used, such as bringing the silane compound into contact with the modification target on which the polymer chains are formed.

In step 3, the addition of the silane compound to the surfaces of the polymer chains is followed by reaction with at least a fluoroalkyl group-containing silane compound to form modified polymer chains.

The fluoroalkyl group of the fluoroalkyl group-containing silane compound may be, for example, a group represented by the following formula:

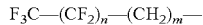

wherein n is 0 to 5 and m is 0 to 8.

In the formula, n is preferably 1 to 5, more preferably 3 to 5; m is preferably 1 to 6, more preferably 2 to 6; and m and n preferably satisfy $0 \leq m+n \leq 10$, more preferably $0 \leq m+n \leq 7$.

Specific examples of the fluoroalkyl group include 3,3,3-trifluoropropyl, 3,3,4,4,4-pentafluorobutyl, 3,3,4,4,5,5,6,6,6-nonafluorohexyl, 3,3,4,4,5,5,6,6,7,7,7-undecafluoroheptyl, and 3,3,4,4,5,5,6,6,7,7,8,8,8-tridecafluorooctyl groups.

In order to cost-effectively provide a variety of functions, including sliding properties, liquid leakage resistance, and protein adsorption resistance, the fluoroalkyl group-containing silane compound may suitably be, but not limited to, a compound represented by the following formula (1):

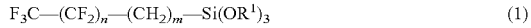

wherein n is 0 to 5; m is 0 to 8; and each $R^1$ may be the same or different and represents an alkyl group.

In formula (1), n is preferably 1 to 5, more preferably 3 to 5; m is preferably 1 to 6, more preferably 2 to 6; and m and n preferably satisfy $0 \leq m+n \leq 10$, more preferably $0 \leq m+n \leq 7$. $R^1$ (alkyl group) may be linear, branched, or cyclic, or a combination of two or more of these structures. The number of carbon atoms of $R^1$ is preferably 1 to 10, more preferably 1 to 5, still more preferably 1 to 3. Examples of the alkyl group for $R^1$ include methyl, ethyl, and propyl groups.

Specific examples of the fluoroalkyl group-containing silane compound of formula (1) include 3,3,3-trifluoropropyltrimethoxysilane, 3,3,3-trifluoropropyltriethoxysilane, 3,3,4,4,5,5,6,6,7,7,8,8,8-tridecafluoro-octyltrimethoxysilane, triethoxy-1H,1H,2H,2H-tridecafluoro-n-octylsilane, and $CF_3(CF_2)_3CH_2CH_2Si(OCH_2CH_3)_3$. These may be used alone or in combinations of two or more.

In step 3, the fluoroalkyl group-containing silane compound may be reacted with (added to) the polymer chains to which the silane compound is added, by any method, and appropriate conventional methods may be used, such as bringing a solution of the fluoroalkyl group-containing silane compound into contact with the modification target in which the silane compound is added to the surfaces of the polymer chains. The solution of the fluoroalkyl group-containing silane compound may be prepared by appropriately adjusting the concentration of the compound in a known solvent which can dissolve the compound, such as water, perfluorohexane, acidic water, methanol, ethanol, or a mixture of water with methanol or ethanol. The contact between the solution and the modification target may be made by any method that brings them into contact with each other, such as application, spraying, or immersion.

The reaction of the fluoroalkyl group-containing silane compound with the polymer chains to which the silane compound is added is preferably further held at a humidity of 50% or higher after the contact (e.g. immersion). This further promotes the reaction so that the effects of the present invention can be well achieved. The humidity is more preferably 60% or higher, still more preferably 80% or higher. The upper limit of the humidity is not particularly critical, but is preferably, for example, 100% or lower. The holding time and temperature may be appropriately chosen and are preferably, for example, 0.5 to 60 hours and 20 to 120° C., respectively.

In a suitable embodiment of step 3, in order to achieve the effects of the present invention well, the addition of the silane compound to the surfaces of the polymer chains may be followed by reaction (addition) of the fluoroalkyl group-containing silane compound as well as a perfluoroether group-containing silane compound to form modified polymer chains.

The perfluoroether group-containing silane compound may be any silane compound containing a perfluoroether group. It may suitably be, for example, a compound represented by the following formula (2) or (3):

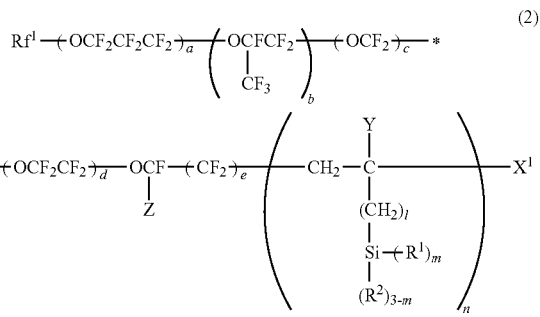

wherein $Rf^1$ is a perfluoroalkyl group; Z is fluorine or a trifluoromethyl group; a, b, c, d, and e are the same as or different from each other and each represent an integer of 0 or 1 or more, provided that a+b+c+d+e is 1 or more and the order of the repeating units parenthesized by subscripts a, b, c, d, and e occurring in the formula is not limited to that shown; Y is hydrogen or a C1-C4 alkyl group; $X^1$ is hydrogen, bromine, or iodine; $R^1$ is a hydroxy group or a hydrolyzable substituent such as a C1-C4 alkoxy group; $R^2$ is hydrogen or a monovalent hydrocarbon group; l is 0, 1, or 2; m is 1, 2, or 3; and n is an integer of 1 or more, provided that the two ends marked by * are directly bonded to each other, or

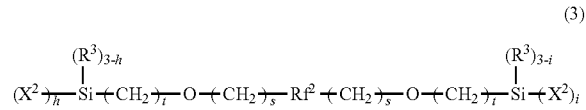

wherein $Rf^2$ is a divalent group that contains a unit represented by —$(C_kF_{2k})O$— where k is an integer of 1 to 6, and has a non-branched linear perfluoropolyalkylene ether structure; each $R^3$ is the same or different and represents a C1-C8 monovalent hydrocarbon group; each $X^2$ is the same or different and represents a hydrolyzable group such as a C1-C4 alkoxy group or a halogen atom; each s is the same or different and represents an integer of 0 to 2; each t is the same or different and represents an integer of 1 to 5; and h and i are the same as or different from each other and each represent 1, 2, or 3.

$Rf^1$ in formula (2) may be any of the perfluoroalkyl groups contained in common organic-containing fluoropolymers, and examples include linear or branched C1-C16 groups. In particular, $CF_3$—, $C_2F_5$— and —$C_3F_7$— are preferred.

In formula (2), each of a, b, c, d, and e represents the number of repeating units in the perfluoropolyether chain which forms the backbone of the fluorine-containing silane compound, and is independently preferably 0 to 200, more preferably 0 to 50. Moreover, a+b+c+d+e (the sum of a to e) is preferably 1 to 100. The order of the repeating units parenthesized by subscripts a, b, c, d, and e occurring in formula (2) is not limited to the order shown, and the repeating units may be joined in any order.

Examples of the C1-C4 alkyl group for Y in formula (2) include methyl, ethyl, propyl, and butyl groups, which may be linear or branched. When $X^1$ is bromine or iodine, the fluorine-containing silane compound easily forms a chemical bond.

Preferred examples of the hydrolyzable substituent for $R^1$ in formula (2) include, but not limited to, halogens, —$OR^4$, —$OCOR^4$, —$OC(R^4)=C(R^5)_2$, —$ON=C(R^4)_2$, and —$ON=CR^6$, where $R^4$ is an aliphatic hydrocarbon group or an aromatic hydrocarbon group, $R^5$ is hydrogen or a C1-C4 aliphatic hydrocarbon group, and $R^6$ is a C3-C6 divalent aliphatic hydrocarbon group. The hydrolyzable substituent is more preferably chlorine, —$OCH_3$, or —$OC_2H_5$. Preferred examples of the monovalent hydrocarbon group for $R^2$ include, but not limited to, methyl, ethyl, propyl, and butyl groups, which may be linear or branched.

In formula (2), l represents the number of carbon atoms of the alkylene group between the carbon in the perfluoropolyether chain and the silicon attached thereto and is preferably 0; and m represents the number of substituents $R^1$ bonded to the silicon to which $R^2$ is bonded through a bond not attached to $R^1$. The upper limit of n is not particularly critical but is preferably an integer of 1 to 10.

In formula (3), the group $Rf^2$ is preferably, but not limited to, such that when each s is 0, the ends of $Rf^2$ group bonded to the oxygen atoms in formula (3) are not oxygen atoms. Moreover, k in $Rf^2$ is preferably an integer of 1 to 4. Specific examples of the group $Rf^2$ include —$CF_2CF_2O$ $(CF_2CF_2CF_2O)_jCF_2CF_2$— where j is an integer of 1 or more, preferably of 1 to 50, more preferably of 10 to 40; and —$CF_2(OC_2F_4)_p$—$(OCF_2)_q$— where p and q are each an integer of 1 or more, preferably of 1 to 50, more preferably of 10 to 40, and the sum of p and q is an integer of 10 to 100, preferably of 20 to 90, more preferably of 40 to 80, and the repeating units ($OC_2F_4$) and ($OCF_2$) are randomly arranged.

$R^3$ in formula (3) is preferably a C1-C8 monovalent hydrocarbon group, and examples include alkyl groups such as methyl, ethyl, propyl, butyl, pentyl, hexyl, heptyl, and octyl groups; cycloalkyl groups such as cyclopentyl and cyclohexyl groups; aryl groups such as phenyl, tolyl, and xylyl groups; aralkyl groups such as benzyl and phenethyl groups; and alkenyl groups such as vinyl, allyl, butenyl, pentenyl, and hexenyl groups. Preferred among these is a methyl group.

Examples of the hydrolyzable group for $X^2$ in formula (3) include alkoxy groups such as methoxy, ethoxy, propoxy, and butoxy groups; alkoxyalkoxy groups such as methoxymethoxy, methoxyethoxy, and ethoxyethoxy groups; alkenyloxy groups such as allyloxy and isopropenoxy groups; acyloxy groups such as acetoxy, propionyloxy, butylcarbonyloxy, and benzoyloxy groups; ketoxime groups such as dimethylketoxime, methylethylketoxime, diethylketoxime, cyclopennoxime, and cyclohexanoxime groups; amino groups such as N-methylamino, N-ethylamino, N-propylamino, N-butylamino, N,N-dimethylamino, N,N-diethylamino, and N-cyclohexylamino groups; amide groups such as N-methylacetamide, N-ethylacetamide, and N-methylbenzamide groups; and aminooxy groups such as N,N-dimethylaminooxy and N,N-diethylaminooxy groups. Examples of the halogen atom for $X^2$ include chlorine, bromine, and iodine atoms. Preferred among these are a methoxy group, an ethoxy group, an isopropenoxy group, and a chlorine atom.

In formula (3), s is preferably 1 and t is preferably 3. In view of hydrolyzability, h and i are each preferably 3.

The perfluoroether group-containing silane compound may also be a compound represented by the following formula (4):

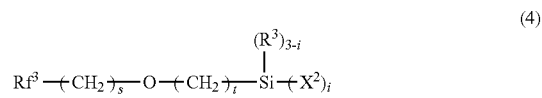

wherein $Rf^3$ is a monovalent group that contains a unit represented by —$(C_kF_{2k})O$— where k is an integer of 1 to 6, and has a non-branched linear perfluoropolyalkylene ether structure; each $R^3$ is the same or different and represents a C1-C8 monovalent hydrocarbon group; each $X^2$ is the same or different and represents a hydrolyzable group such as a C1-C4 alkoxy group or a halogen atom; s represents an integer of 0 to 2; t represents an integer of 1 to 5; and i represents 1, 2, or 3.

In formula (4), the group $Rf^3$ is preferably, but not limited to, such that when s is 0, the end of $Rf^3$ group bonded to the oxygen atom in formula (4) is not an oxygen atom. Moreover, k in $Rf^3$ is preferably an integer of 1 to 4. Specific examples of the group $Rf^3$ include $CF_2CF_2O(CF_2CF_2$ $CF_2O)_jCF_2CF_2$— where j is an integer of 1 or more, preferably of 1 to 50, more preferably of 10 to 40; and $CF_3(OC_2F_4)_p$—$(OCF_2)_q$— where p and q are each an integer of 1 or more, preferably of 1 to 50, more preferably of 10 to 40, and the sum of p and q is an integer of 10 to 100, preferably of 20 to 90, more preferably of 40 to 80, and the repeating units ($OC_2F_4$) and ($OCF_2$) are randomly arranged.

Examples of $R^3$ in formula (4) include those mentioned for $R^3$ in formula (3). Examples of $X^2$ in formula (4) include those mentioned for $X^2$ in formula (3). In formula (4), s is preferably 1 and t is preferably 3. In view of hydrolyzability, i in formula (4) is preferably 3.

For durable mold-releasing effect, the perfluoroether group-containing silane compound preferably has an average molecular weight of 1,000 to 10,000. The average molecular weight may be determined by gel permeation chromatography (GPC) calibrated with polystyrene standards.

Commercial products of the perfluoroether group-containing silane compound include OPTOOL DSX (Daikin Industries, Ltd.), KY-108 and KY-164 (Shin-Etsu Chemical Co., Ltd.), Fluorolink S10 (Solvay Specialty Polymers Japan K.K.), Novec 2702 and Novec 1720 (3M Japan Limited), and FLUOROSURF series such as FLUOROSURF FG-5080SH (Fluoro Technology), and SIP6720.72 (Gelest, [perfluoro(polypropyleneoxy)]methoxypropyltrimethoxysilane, $CF_3CF_2CF_2O(CF_2CF_2CF_2O)_nCH_2OCH_2CH_2CH_2Si$ $(OCH_3)_3$).

In step 3, the perfluoroether group-containing silane compound may further be reacted (added) by any method, e.g., as described for the fluoroalkyl group-containing silane compound but using a solution containing a perfluoroether group-containing silane compound in addition to a fluoroalkyl group-containing silane compound instead of the solution of a fluoroalkyl group-containing silane compound.

In step 3, in order to provide a variety of functions, including sliding properties, liquid leakage resistance, and protein adsorption resistance, the fluoroalkyl group-containing silane compound and the perfluoroether group-containing silane compound are preferably combined in a ratio (mass ratio of fluoroalkyl group-containing silane compound/perfluoroether group-containing silane compound) of 50:50 to 100:0, more preferably 60:40 to 90:10, still more preferably 65:35 to 85:15.

A second aspect of the present invention relates to a method for surface-modifying a rubber vulcanizate as a modification target, which includes: step I of radically polymerizing a monomer in the presence of a photopolymerization initiator A on the surface of the modification target to grow polymer chains; and step II of adding a silane compound to the surfaces of the polymer chains, followed by reaction with at least a fluoroalkyl group-containing silane compound to form modified polymer chains.

Specifically, the second aspect of the present invention provides a surface modification method that includes radically polymerizing a monomer using a photopolymerization initiator A as an initiator to form polymer chains, then adding a silane compound to the polymer chains, and further reacting (e.g. adding) at least a fluoroalkyl group-containing silane compound with the surface of the silane compound to form modified polymer chains, whereby the fluoroalkyl group-containing functional silane compound is provided on the outermost surface. Thus, desired functions can be provided very cost-effectively. Further, the attachment of at least a fluoroalkyl group-containing functional silane compound to the outermost surface provides desired functions such as high sliding properties, liquid leakage resistance, biocompatibility, and protein adsorption resistance.

Preferably, step I includes radically polymerizing a monomer starting from polymerization initiation points A formed from a photopolymerization initiator A on the surface of the modification target to grow polymer chains, and step II includes adding a silane compound to the surfaces of the polymer chains, followed by reaction with at least a fluoroalkyl group-containing silane compound to add the functional silane compound, thereby forming modified polymer chains. For example, step I may be carried out by bringing a photopolymerization initiator A and a monomer into contact with the surface of the modification target, followed by irradiation with LED light having a wavelength of 300 to 400 nm to create polymerization initiation points A from the photopolymerization initiator A while radically polymerizing the monomer starting from the polymerization initiation points A to grow polymer chains; and step II may be carried out by bringing a silane compound into contact with the surfaces of the polymer chains, and further reacting (e.g. adding) at least a fluoroalkyl group-containing silane compound with the surface of the silane compound so that the fluoroalkyl group-containing functional silane compound is provided on the outermost surface.

The method for radical polymerization of the monomer, the solvent for application (spraying), the method for application (spraying), the method for immersion, the conditions for irradiation, and other conditions used in step I may be those described in WO 2016/042912, which is hereby incorporated by reference.

The reaction (e.g. addition) of the silane compound or fluoroalkyl group-containing silane compound in step II may be performed as described for step 3.

In a suitable embodiment of step II, in order to achieve the effects of the present invention well, the addition of the silane compound to the surfaces of the polymer chains may be followed by reaction (addition) of the fluoroalkyl group-containing silane compound as well as the aforementioned perfluoroether group-containing silane compound to form modified polymer chains. The reaction (addition) may be carried out as described above. Moreover, the suitable ratio of the fluoroalkyl group-containing silane compound and the perfluoroether group-containing silane compound combined in step II is the same as that mentioned above.

The length (total thickness) of the resulting modified polymer chain (graft chain+silane compound+fluoroalkyl group-containing silane compound) is preferably 200 to 7000 nm, more preferably 500 to 3000 nm. When the length is shorter than 200 nm, good sliding properties tend not to be achieved. When the length is longer than 7000 nm, a further improvement in sliding properties cannot be expected while the cost of raw materials tends to increase due to the use of the expensive monomer. In addition, surface patterns generated by the surface treatment tend to be visible to the naked eyes and spoil the appearance, and also to decrease sealing properties.

In step 2 and step I, two or more monomers may simultaneously be radically polymerized starting from the polymerization initiation points A. In step 3 and step II, two or more silane compounds may simultaneously be added, and two or more fluoroalkyl group-containing silane compounds or perfluoroether group-containing silane compounds may simultaneously be reacted with the surface of the added silane compound(s). Moreover, the polymer chains, silane compound, and other compounds may each be stacked in two or more layers. Furthermore, multiple types of polymer chains may be grown on the surface of the modification target. In the surface modification methods of the present invention, the polymer chains may be crosslinked to one another. In this case, the polymer chains may be crosslinked to one another by ionic crosslinking, crosslinking by a hydrophilic group containing an oxygen atom, crosslinking by a halogen group such as iodine, or crosslinking by UV, electron beams, y rays, or other radiation.

The surface modification methods may be applied to rubber vulcanizates to produce surface-modified elastic bodies. For example, surface-modified elastic bodies that are excellent in sliding properties in the presence of water or in a dry state can be obtained. Such surface-modified elastic bodies are also excellent in that they have low friction and low water resistance or drag. Moreover, the methods may be applied to at least a part of a three-dimensional solid body (e.g. elastic body) to produce a surface-modified elastic body with modified properties. Furthermore, preferred examples of such surface-modified elastic bodies include polymer brushes. The term "polymer brush" means an assembly of graft polymer molecules obtained in the "grafting from" approach by surface-initiated living radical polymerization. The graft chains are preferably oriented in a direction substantially vertical to the surface of the modification target because then the entropy is reduced so that the molecular mobility of the graft chains decreases, thus providing sliding properties. Moreover, semidilute or concentrated brushes having a brush density of 0.01 chains/nm$^2$ or higher are preferred.

The surface modification methods may also be applied to rubber vulcanizates to produce gaskets for syringes at least part of whose surface is modified. Preferably, at least the sliding portion of the surface of the gaskets is modified. The entire surface of the gaskets may be modified.

Suitable examples of the gaskets for syringes include a gasket for syringes which includes a gasket base material with the polymer chains fixed on at least part of the surface thereof, and has a sliding surface provided with a plurality of annular projections, wherein the annular projections include a first projection nearest to the top surface of the gasket, and the first projection has a surface roughness Ra of not greater than 1.0. Since modified polymer chains are fixed on the surface of the base material, and further the surface roughness Ra of at least the first projection located nearest to the top surface is adjusted to not greater than 1.0, high sliding properties and high liquid leakage resistance can be simultaneously achieved.

Figure 2:
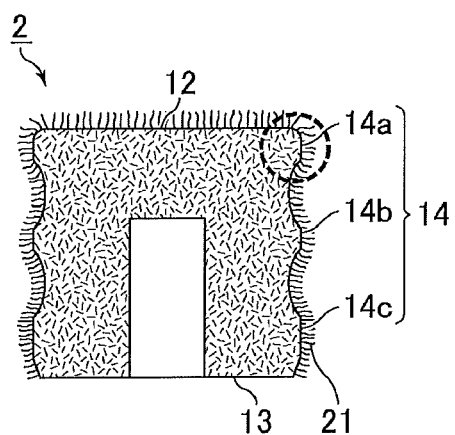
FIG. 2 is an example of a longitudinal sectional view of a gasket for syringes in which modified polymer chains are fixed on the surface of the gasket base material.
Figure 3:
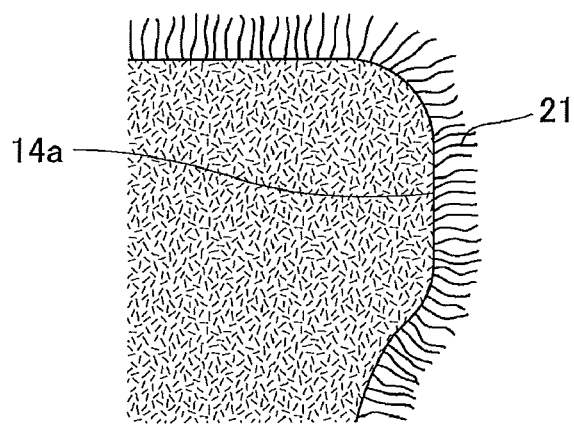
FIG. 3 is an example of a partially enlarged view of the first projection of the gasket for syringes of FIG. 2.

FIG. 1 is an example of a longitudinal sectional view (cross-sectional view in the sliding direction, longitudinal profile) of a base material 1 (gasket base material 1) on which modified polymer chains are to be fixed. FIG. 2 is an example of a longitudinal sectional view of a gasket for syringes 2 in which modified polymer chains 21 are fixed on the surface of the gasket base material 1 shown in FIG. 1. FIG. 3 is an example of a partially (area enclosed by the circle) enlarged view of a first projection 14a of the gasket for syringes 2 shown in FIG. 2.

The gasket for syringes 2 may be used in, for example, a syringe that includes a barrel into which liquid is to be injected, a plunger for pushing the injected liquid out of the barrel, and a gasket attached to the tip of the plunger.

The gasket for syringes 2 of FIG. 2 is one in which modified polymer chains are fixed on at least part of the sliding surface of the gasket base material 1 of FIG. 1. In the cylindrical gasket base material 1 and the gasket for syringes 2 in which modified polymer chains 21 are fixed on the gasket base material 1, the circumferences of the top surface 12 on the liquid-contact side and of the bottom surface 13 to be connected to the tip of a plunger are integrated with a sliding portion 14 (cylindrical portion) extending in the height direction (sliding direction).

With regard to the gasket base material 1 and the gasket for syringes 2, the outer periphery of the sliding portion 14 includes three annular projections that make a sliding contact with the inner periphery of the cylindrical portion of the barrel; specifically, a first projection 14a at a position nearest to the top surface 12 (first projection 14a nearest to the top surface), a bottom-side projection 14c at a position farthest from the top surface 12 (bottom-side projection 14c nearest to the bottom surface), and an intermediate projection 14b at a position between the projections 14a and 14c. In the gasket base material of FIG. 1, the top surface 12 is integrated with the first projection 14a.

Although FIGS. 1 and 2 show embodiments having three annular projections, there may be any number, but at least two, of annular projections. Although the embodiments have one intermediate projection 14b, any projection between the first projection and the bottom-side projection corresponds to an intermediate projection, and there may be a plurality of intermediate projections.

In order to simultaneously achieve sliding properties and liquid leakage resistance, the gasket for syringes 2 preferably has three or more annular projections. In the cylindrical gasket base material 1 and the gasket for syringes 2, the top surface 12 on the liquid-contact side, the bottom surface 13 to be connected to the tip of a plunger, the first projection 14a, the intermediate projection 14b, the bottom-side projection 14c, and the sliding portion 14 may each have any shape.

The gasket for syringes 2 of FIGS. 2 and 3 (the partially enlarged view of the first projection 14a) is one in which modified polymer chains 21 are fixed on at least part of the surface of the gasket base material 1. These figures show an example in which modified polymer chains 21 are fixed on the top surface 12 and the entire sliding portion 14 (cylindrical portion) including the annular projections (first projection 14a, intermediate projection 14b, and bottom-side projection 14c).

In the gasket for syringes 2 (after modified polymer chains are fixed thereon), the first projection 14a provided with modified polymer chains 21 preferably has a surface roughness Ra of not greater than 1.0, more preferably not greater than 0.8, still more preferably not greater than 0.6, in order to simultaneously achieve sliding properties and liquid leakage resistance. The lower limit of the Ra is not particularly critical, and a smaller Ra is better.

The term "surface roughness Ra" as used herein refers to the arithmetic average height Ra defined in JIS B 0601-2001 or ISO 4287-1997.

In the gasket base material 1 (before modified polymer chains are fixed thereon), the first projection 14a preferably has a surface roughness Ra of not greater than 1.0, more preferably not greater than 0.8, still more preferably not greater than 0.6, in order to simultaneously achieve sliding properties and liquid leakage resistance. The lower limit of the Ra is not particularly critical, and a smaller Ra is better.

In the gasket for syringes 2 (after modified polymer chains are fixed thereon), the first projection 14a provided with modified polymer chains 21 preferably has a surface roughness Rz of not greater than 25.0, more preferably not greater than 22.0, still more preferably not greater than 20.0, in order to simultaneously achieve sliding properties and liquid leakage resistance. The lower limit of the Rz is not particularly critical, and a smaller Rz is better.

The term "surface roughness Rz" as used herein refers to the maximum height Rz defined in JIS B 0601-2001 or ISO 4287-1997.

In the gasket for syringes 2 (after modified polymer chains are fixed thereon), the first projection 14a provided with modified polymer chains 21 preferably has a surface roughness Rv of not greater than 21.0, more preferably not greater than 18.0, still more preferably not greater than 16.5, in order to simultaneously achieve sliding properties and liquid leakage resistance. The lower limit of the Rv is not particularly critical, and a smaller Rv is better.

The term "surface roughness Rv" as used herein refers to the maximum valley depth Rv defined in JIS B 0601-2001 or ISO 4287-1997.

The surface roughness Ra of the gasket base material 1 and the gasket for syringes 2 in which modified polymer chains 21 are fixed on the gasket base material 1 may be controlled, for example, by changing the surface roughness of the forming mold. Specifically, it may be controlled by changing the particle size of the abrasive used in the final finishing step in the preparation of the mold.

Examples of the abrasive include abrasive grains of diamond, alumina, silicon carbide, cubic boron nitride, boron carbide, zirconium oxide, manganese oxide, and colloidal silica. The abrasives #46 to 100 defined in JIS R 6001-1998 may be suitably used.

The material of the forming mold may be a known material, such as carbon steel or precipitation stainless steel. The forming mold may be prepared by cutting methods such as by cutting with a cemented carbide tool, coated cemented carbide, sintered cBN, or other tools, followed by polishing and finishing processes.

The surface roughness Rz or Rv of the gasket for syringes 2 with modified polymer chains 21 fixed thereon may be controlled by varying the drying method performed after the surface reacted with a fluoroalkyl group-containing silane compound is washed with a solvent such as acetone. Specifically, the above-indicated Rz or Rv range may be obtained by drying the surface at normal pressure without rapidly drying it, followed by gradual drying, e.g. in vacuo, to reduce the Rz or Rv, because if only the modified polymer chains are rapidly dried after washing, the surface tends to crack and show an increased Rz or Rv.

EXAMPLES

The present invention will be specifically described below with reference to, but not limited to, examples.

The rubber vulcanizates (gasket base materials of the form shown in FIG. 1) used in the following examples and comparative examples were prepared by crosslinking (vulcanizing at 180° C. for 10 minutes) an isoprene unit-containing chlorobutyl rubber (degree of unsaturation: 1 to 2%) by triazine. In the preparation, the amount of the filler and the amount of triazine were varied to adjust the hardness of the rubber vulcanizates, whereby gaskets having a Shore A hardness of 47, 50.5, 54, 57, 63, or 72 were prepared (the hardness was determined as described below).

Since it was difficult to determine the hardness of the rubber vulcanizates (gasket base materials), corresponding rubber vulcanizate sheets were prepared using the same composition and vulcanization conditions, and the hardness of the sheets was measured and used as the hardness of the gasket base materials (the hardness of the gasket base materials can be considered the same as that of the respective sheets).

[Hardness of Rubber Vulcanizate (Gasket Base Material)]

The hardness (Shore A) of the rubber vulcanizates (gasket base materials) at 23° C. was determined using a type-A durometer according to JIS K 6253 "Rubber, vulcanized or thermoplastic—Determination of hardness".

Example 1

A rubber vulcanizate (gasket base material) was immersed in a 1 wt % solution of benzophenone in acetone so that benzophenone was adsorbed onto the surface of the rubber vulcanizate, followed by drying. The dried rubber vulcanizate (gasket base material) was immersed in an aqueous solution mixture containing acrylic acid and acrylamide in a ratio of 25:75 (2.5 M, 4.5 g of acrylic acid and 13.4 g of acrylamide dissolved in 100 mL of water) in a glass reaction vessel, followed by irradiation with LED-UV light having a wavelength of 365 nm for 50 minutes to cause radical polymerization so that polymer chains were grown on the rubber surface. Thereafter, the surface was washed with water and dried.

Next, the dried rubber vulcanizate was immersed in a 1 wt % solution of a silane compound (Primer coat PC-3B, Fluoro Technology, the butoxy/ethoxy tetraalkoxysilane of the above formula) in butanol and taken out therefrom. The rubber vulcanizate was then left at a humidity of 90% and a temperature of 100° C. for two hours to cause a reaction. The surface was washed with acetone and then water and dried.

The dried rubber vulcanizate (gasket base material) was immersed in a 2% perfluorohexane solution containing a fluoroalkyl group-containing silane compound represented by the following formula (triethoxy-1H,1H,2H,2H-tridecafluoro-n-octylsilane: T1770, Tokyo Chemical Industry Co., Ltd., fluoroalkyl group: $CF_3(CF_2)_5(CH_2)_2$—) and a perfluoroether group-containing silane compound (Daikin Industries, Ltd., OPTOOL DSX-E, a compound of formula (2)) in a ratio of 100:0 (by mass) and taken out therefrom. Thereafter, the rubber vulcanizate was left at a humidity of 90% and a temperature of 70° C. for eight hours to cause a reaction. The resulting rubber vulcanizate was washed with acetone and dried. Thus, a surface-modified elastic body was prepared.

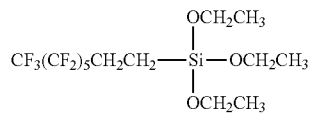

Examples 2 to 17 and Comparative Example 2

A surface-modified elastic body was prepared in the same manner as in Example 1, except that the hardness of the rubber vulcanizate (gasket base material), the ratio of acrylic acid and acrylamide combined, and the ratio of the fluoroalkyl group-containing silane compound and the perfluoroether group-containing silane compound combined were changed as listed in Table 1.

Example 18

A surface-modified elastic body was prepared in the same manner as in Example 15, except that the fluoroalkyl group-containing silane compound was changed to $CF_3(CF_2)_3CH_2CH_2Si(OCH_2CH_3)_3$—

Comparative Example 1

A rubber vulcanizate (gasket base material) prepared by crosslinking (vulcanizing at 180° C. for 10 minutes) an isoprene unit-containing chlorobutyl rubber (degree of unsaturation: 1 to 2%) by triazine was used as it was (Shore A hardness: 50.5).

In Examples 4 and 17 of Table 2, in the drying step after the reaction (addition) of the fluoroalkyl group-containing silane compound and subsequent washing with acetone, the rubber vulcanizate was dried naturally at normal pressure for two hours or more and then heated to 120° C. over two hours or more in an oven. Then, evacuation was started and maintained for one hour for drying.

The surface-modified elastic bodies prepared in the examples and comparative examples were evaluated as described below.

[Surface Roughness Ra, Rz, Rv]

The Ra (arithmetic average height), Rz (maximum height), and Rv (maximum valley depth) of the rubber vulcanizates (gasket base materials) and surface-modified elastic bodies (after fixation of modified polymer chains) were determined according to JIS B 0601-2001 (ISO 4287-1997).

(Length of Modified Polymer Chain (Total Polymer Chain Length))

To determine the length of the modified polymer chain formed on the surface of the rubber vulcanizates, cross-sections of the modified rubber vulcanizates on which modified polymer chains were formed were measured with an SEM at an accelerating voltage of 15 kV and a magnification of 1000 times. The thickness of the polymer layer photographed was determined and used as the length of the modified polymer chain.

(Sliding Properties (Friction Resistance))

To determine the friction resistance of the surface of the rubber vulcanizate (gasket base material) and surface-modified elastic bodies prepared in the examples and comparative examples, they were inserted into a COP resin barrel of a syringe and then pushed towards the end of the barrel using a tensile tester (push rate: 30 mm/min) while friction resistance was measured. The friction resistance of each example is expressed as a friction resistance index using the equation below, with Comparative Example 1 set equal to 100. A lower index indicates a lower friction resistance and better sliding properties.

(Friction resistance index)=(Friction resistance of each example)/(Friction resistance of Comparative Example 1)×100

(Liquid Leakage Resistance)

The vulcanized rubber gaskets prepared in the examples and comparative examples were inserted into a COP resin barrel of a syringe. A solution of red food coloring in water was introduced into the barrel, and the barrel was sealed with a cap. After two-week storage at 40° C., the barrel was visually observed for liquid leakage and evaluated using the following four-point scale.

Excellent: no red (pink) stain of red food coloring was observed in the first projection nearest to the top surface.

Good: A slight red (pink) stain of red food coloring was observed in the upper half of the first projection nearest to the top surface.

Fair: A red (pink) stain of red food coloring was observed down to the bottom of the first projection nearest to the top surface.

Poor: A red (pink) stain of red food coloring was observed beyond the first projection nearest to the top surface.

(Amount of Proteins Adsorbed)

The surface of the prepared samples (rubber vulcanizate (gasket base material) and surface-modified elastic bodies) was brought into contact with a 1 mg/ml solution of bovine serum albumin (BSA) and left at 37° C. for three hours. The surface of the samples was lightly washed with phosphate-buffered saline to prepare protein-adsorbed samples. The entire amount of each protein-adsorbed sample was put into a 50-ml centrifuge tube, and the proteins adsorbed on the surface of the samples were extracted in accordance with the method described in Section 3.6: Water-soluble proteins of JIS T 9010:1999 "Test methods relevant to biological safety of rubber products." To the extracted proteins was accurately added 0.5 ml of a 0.1 mol/l aqueous solution of sodium hydroxide to dissolve the proteins. Thus, sample solutions were prepared. Also, a procedural blank was prepared by following the same procedure, but adding no sample.

A volume of 0.2 ml each of the sample solutions and reference solutions (5 to 100 µg/ml BSA solutions) was accurately weighed and assayed for protein amount by the Lowry method. A calibration curve was prepared from the BSA concentrations (µg/ml) and absorbances of the reference solutions, and used to calculate the protein concentration (µg/ml) per milliliter of the sample solution, which was calculated per area of the rubber vulcanizate (gasket base material) or surface-modified elastic body.

TABLE 1

| | Comp. Ex. 1 | Ex. 1 | Ex. 2 | Ex. 3 | Ex. 4 | Ex. 5 | Ex. 6 | Ex. 7 | Ex. 8 |
|---|---|---|---|---|---|---|---|---|---|
| Acrylamide/acrylic acid | — | 75/25 | 75/25 | 75/25 | 75/25 | 75/25 | 75/25 | 75/25 | 75/25 |
| Silane compound (PC-3B) | — | Present | Present | Present | Present | Present | Present | Present | Present |
| Fluoroalkyl group-containing silane compound (T1770)/perfluoroether group-containing silane compound (DSX-E) | — | 100/0 | 85/15 | 75/25 | 65/35 | 55/45 | 75/25 | 75/25 | 75/25 |
| Fluoroalkyl group-containing silane compound ($CF_3(CF_2)_3CH_2CH_2Si(OCH_2CH_3)_3$)/perfluoroether group-containing silane compound (DSX-E) | — | — | — | — | — | — | — | — | — |
| Hardness (Shore A) | 50.5 | 50.5 | 50.5 | 50.5 | 50.5 | 50.5 | 54 | 57 | 63 |
| Surface roughness Ra (gasket base material) | 0.3 | 0.3 | 0.3 | 0.3 | 0.3 | 0.3 | 0.25 | 0.25 | 0.2 |
| Surface roughness Ra (after fixation of modified polymer chains) | — | 0.6 | 0.55 | 0.55 | 0.55 | 0.5 | 0.5 | 0.5 | 0.45 |
| Sliding properties | 100 | 1.735 | 1.5525 | 1.4425 | 1.41 | 1.36 | 0.89 | 0.9075 | 1.38 |
| Liquid leakage resistance | Fair | Good | Excellent | Excellent | Excellent | Good | Excellent | Excellent | Excellent |
| Amount of proteins adsorbed (µg/cm$^2$) | 1.62 | 0.34 | 0.37 | 0.38 | 0.45 | 0.62 | 0.35 | 0.32 | 0.33 |
| Length of modified polymer chain (nm) | 0 | 550 | 600 | 630 | 640 | 645 | 630 | 630 | 635 |

| | Ex. 9 | Ex. 10 | Ex. 11 | Ex. 12 | Ex. 13 | Ex. 14 |
|---|---|---|---|---|---|---|
| Acrylamide/acrylic acid | 75/25 | 75/25 | 75/25 | 75/25 | 90/10 | 65/35 |
| Silane compound (PC-3B) | Present | Present | Present | Present | Present | Present |
| Fluoroalkyl group-containing silane compound (T1770)/perfluoroether group-containing silane compound (DSX-E) | 55/45 | 55/45 | 55/45 | 55/45 | 65/35 | 65/35 |
| Fluoroalkyl group-containing silane compound ($CF_3(CF_2)_3CH_2CH_2Si(OCH_2CH_3)_3$)/perfluoroether group-containing silane compound (DSX-E) | — | — | — | — | — | — |
| Hardness (Shore A) | 50.5 | 54 | 57 | 63 | 57 | 57 |
| Surface roughness Ra (gasket base material) | 0.3 | 0.25 | 0.25 | 0.2 | 0.25 | 0.25 |
| Surface roughness Ra (after fixation of modified polymer chains) | 0.6 | 0.55 | 0.55 | 0.5 | 0.45 | 0.5 |
| Sliding properties | 1.245 | 0.9125 | 1.4425 | 1.665 | 0.97 | 0.8275 |
| Liquid leakage resistance | Good | Good | Excellent | Excellent | Excellent | Excellent |
| Amount of proteins adsorbed (µg/cm$^2$) | 0.51 | 0.48 | 0.46 | 0.57 | 0.4 | 0.41 |
| Length of modified polymer chain (nm) | 735 | 745 | 750 | 750 | 480 | 680 |

TABLE 1-continued

|  | Ex. 15 | Ex. 16 | Ex. 17 | Comp. Ex. 2 | Ex. 18 |
|---|---|---|---|---|---|
| Acrylamide/acrylic acid | 50/50 | 25/75 | 0/100 | 75/25 | 50/50 |
| Silane compound (PC-3B) | Present | Present | Present | Present | Present |
| Fluoroalkyl group-containing silane compound (T1770)/ perfluoroether group-containing silane compound (DSX-E) | 65/35 | 65/35 | 65/35 | 0/100 | — |
| Fluoroalkyl group-containing silane compound $(CF_3(CF_2)_3CH_2CH_2Si(OCH_2CH_3)_3)$/ perfluoroether group-containing silane compound (DSX-E) | — | — | — | — | 65/35 |
| Hardness (Shore A) | 57 | 57 | 57 | 50.5 | 57 |
| Surface roughness Ra (gasket base material) | 0.25 | 0.25 | 0.25 | 0.3 | 0.25 |
| Surface roughness Ra (after fixation of modified polymer chains) | 0.5 | 0.55 | 0.6 | 0.35 | 0.55 |
| Sliding properties | 0.78 | 0.7425 | 0.69 | 0.97 | 2.12 |
| Liquid leakage resistance | Excellent | Excellent | Excellent | Good | Excellent |
| Amount of proteins adsorbed ($\mu g/cm^2$) | 0.43 | 0.43 | 0.48 | 1.41 | 0.52 |
| Length of modified polymer chain (nm) | 780 | 900 | 1200 | 900 | 720 |

TABLE 2

|  | Example 4 | Example 17 |
|---|---|---|
| Acrylamide/acrylic acid | 75/25 | 0/100 |
| Silane compound (PC-3B) | Present | Present |
| Fluoroalkyl group-containing silane compound (T1770)/perfluoroether group-containing silane compound (DSX-E) | 65/35 | 65/35 |
| Fluoroalkyl group-containing silane compound $(CF_3(CF_2)_3CH_2CH_2Si(OCH_2CH_3)_3)$/ perfluoroether group-containing silane compound (DSX-E) | — | — |
| Hardness (Shore A) | 50.5 | 57 |
| Surface roughness Rz (after fixation of modified polymer chains) | 21.6 | 19.8 |
| Surface roughness Rv (after fixation of modified polymer chains) | 15.8 | 15.4 |
| Sliding properties | 1.41 | 0.69 |
| Liquid leakage resistance | Excellent | Excellent |
| Amount of proteins adsorbed ($\mu g/cm^2$) | 0.45 | 0.48 |
| Length of modified polymer chain (nm) | 640 | 1200 |

Tables 1 and 2 show that the surfaces of the surface-modified elastic bodies of the examples exhibited greatly reduced friction resistances and thus good sliding properties. They also showed good liquid leakage resistance and good protein adsorption resistance. In particular, when a silane compound including 50 mass % or more of a fluoroalkyl group-containing silane compound was reacted with (added to) the surface, very high liquid leakage resistance was achieved. Regarding the protein adsorption resistance, if the amount of proteins adsorbed exceeds 1.0 μg/cm², this means that the adsorption of proteins proceeds to multilayer coverage and is thus considered dominant. In the examples, in contrast, the amount of proteins adsorbed was not more than 0.7 μg/cm², which means that the proteins are adsorbed in substantially a monolayer and their adsorption occurs simultaneously with their desorption and is thus not dominant but kept at a good level, i.e., the adsorption does not increase any more. In Comparative Example 2 in which only a perfluoroether group-containing silane compound was used, the amount of proteins adsorbed was as much as 1.41 μg/cm² and the adsorption was considered dominant.

Thus, when these surface-modified elastic bodies are used as gaskets for syringe plungers, they provide sufficient liquid leakage resistance while reducing the friction of the plunger against the syringe barrel, thereby enabling easy and accurate treatment with syringes. They also provide sufficiently reduced protein adsorption.

Furthermore, the above-mentioned effects can also be expected when modified polymer chains are formed on the surface of the grooves formed on the tread or of the sidewalls of tires for use on vehicles such as passenger cars, on the surface of diaphragms, on the sliding surface of skis or snowboards, or on the surface of swimsuits, road signs, or sign boards, for example.

REFERENCE SIGNS LIST

1: gasket base material (before modified polymer chains are fixed thereon)
2: gasket for syringes (after modified polymer chains are fixed thereon)
12: top surface
13: bottom surface
14: sliding portion (cylindrical portion)
14a: first projection
14b: intermediate projection
14c: bottom-side projection
21: modified polymer chain

The invention claimed is:
1. A method for surface-modifying a rubber vulcanizate as a modification target, the method comprising:
  step 1 of forming polymerization initiation points A on a surface of the modification target;
  step 2 of radically polymerizing a monomer starting from the polymerization initiation points A to grow polymer chains; and
  step 3 of bringing a silane compound into contact with the surface of the polymer chain modified rubber vulcanizate, followed by reaction with at least a fluoroalkyl group-containing silane compound to form modified polymer chains;
  wherein the monomer is at least one selected from the group consisting of acrylic acid, acrylic acid esters, alkali metal salts of acrylic acid, amine salts of acrylic acid, acrylamide, dimethylacrylamide, diethylacrylamide, isopropylacrylamide, hydroxyethylacrylamide, acryloylmorpholine, methoxymethyl acrylate, hydroxyethyl acrylate, methacrylic acid, methacrylic acid esters, alkali metal salts of methacrylic acid, amine salts of methacrylic acid, methacrylamide, dimethylmethacrylamide, diethylmethacrylamide, isopropylmethacrylamide, hydroxyethylmethacrylamide, methacryloylmorpholine, methoxymethyl methacrylate, hydroxyethyl methacrylate, and acrylonitrile, and
  wherein step 3 includes the reaction with at least the fluoroalkyl group-containing silane compound and a perfluoroether group-containing silane compound to form the modified polymer chains.

2. A method for surface-modifying a rubber vulcanizate as a modification target, the method comprising:
   step I of radically polymerizing a monomer in the presence of a photopolymerization initiator A on a surface of the modification target to grow polymer chains; and
   step II of bringing a silane compound into contact with the surface of the polymer chain modified rubber vulcanizate, followed by reaction with at least a fluoroalkyl group-containing silane compound to form modified polymer chains;
   wherein the monomer is at least one selected from the group consisting of acrylic acid, acrylic acid esters, alkali metal salts of acrylic acid, amine salts of acrylic acid, acrylamide, dimethylacrylamide, diethylacrylamide, isopropylacrylamide, hydroxyethylacrylamide, acryloylmorpholine, methoxymethyl acrylate, hydroxyethyl acrylate, methacrylic acid, methacrylic acid esters, alkali metal salts of methacrylic acid, amine salts of methacrylic acid, methacrylamide, dimethylmethacrylamide, diethylmethacrylamide, isopropylmethacrylamide, hydroxyethylmethacrylamide, methacryloylmorpholine, methoxymethyl methacrylate, hydroxyethyl methacrylate, and acrylonitrile, and
   wherein step II includes the reaction with at least the fluoroalkyl group-containing silane compound and a perfluoroether group-containing silane compound to form the modified polymer chains.

3. The method according to claim 1,
   wherein the fluoroalkyl group-containing silane compound and the perfluoroether group-containing silane compound are combined in a ratio of 50:50 to 100:0.

4. The method according to claim 1, wherein the fluoroalkyl group is represented by the following formula:

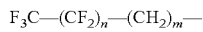

wherein n is an integer of 0 to 5 and m is an integer of 0 to 8.

5. The method according to claim 1,
   wherein the rubber vulcanizate has a Shore A hardness of 50 to 70.

6. The method according to claim 1,
   wherein the rubber vulcanizate has a Shore A hardness of 53 to 65.

7. The method according to claim 1,
   wherein the fluoroalkyl group-containing silane compound is represented by the following formula (1):

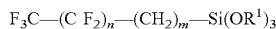 (1)

wherein n is 0 to 5; m is 0 to 8; and each $R^1$ may be the same or different and represents an alkyl group.

8. The method according to claim 1,
   wherein the perfluoroether group-containing silane compound is represented by the following formula (2) or (3):

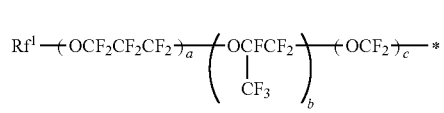 (2)

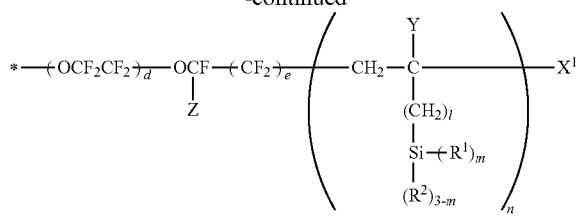

wherein $Rf^1$ is a perfluoroalkyl group; Z is fluorine or a trifluoromethyl group; a, b, c, d, and e are the same as or different from each other and each represent an integer of 0 or 1 or more, provided that a+b+c+d+e is 1 or more and the order of the repeating units parenthesized by subscripts a, b, c, d, and e occurring in the formula is not limited to that shown; Y is hydrogen or a C1-C4 alkyl group; $X^1$ is hydrogen, bromine, or iodine; $R^1$ is a hydroxy group or a hydrolyzable substituent; $R^2$ is hydrogen or a monovalent hydrocarbon group; l is 0, 1, or 2; m is 1, 2, or 3; and n is an integer of 1 or more provided that the two ends marked by * are directly bonded to each other, or

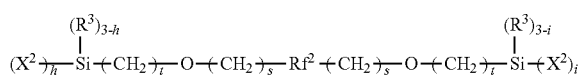 (3)

wherein $Rf^2$ is a divalent group that contains a unit represented by $-(C_kF_{2k})O-$ where k is an integer of 1 to 6, and has a non-branched linear perfluoropolyalkylene ether structure; each $R^3$ is the same or different and represents a C1-C8 monovalent hydrocarbon group; each $X^2$ is the same or different and represents a hydrolyzable group or a halogen atom; each s is the same or different and represents an integer of 0 to 2; each t is the same or different and represents an integer of 1 to 5; and h and i are the same as or different from each other and each represent 1, 2, or 3.

9. The method according to claim 1,
   wherein the modified polymer chains have a length of 200 to 7000 nm.

10. A surface-modified elastic body, comprising
    a three-dimensional solid body at least part of whose surface is modified by the method according to claim 1.

11. A gasket for syringes, at least part of whose surface is modified by the method according to claim 1.

12. The method according to claim 1, wherein the reaction of the fluoroalkyl group-containing silane compound with the polymer chains to which the silane compound is added is held at a humidity of 50% or higher.

13. The method according to claim 2, wherein the reaction of the fluoroalkyl group-containing silane compound with the polymer chains to which the silane compound is added is held at a humidity of 50% or higher.

* * * * *